US011465970B2

(12) United States Patent
Xu

(10) Patent No.: US 11,465,970 B2
(45) Date of Patent: Oct. 11, 2022

(54) METHOD FOR SYNTHESIS OF ROXADUSTAT AND INTERMEDIATE COMPOUNDS THEREOF

(71) Applicants: Nanjing Cavendish Bio-Engineering Technology Co., Ltd., Nanjing (CN); Yongxiang Xu, Nanjing (CN)

(72) Inventor: Yongxiang Xu, Nanjing (CN)

(73) Assignees: Nanjing Cavendish Bio-Engineering Tech. Co., LTD., Nanjing (CN); Yongxiang Xu, Nanjing (CN)

( * ) Notice: Subject to any disclaimer, the term of this patent is extended or adjusted under 35 U.S.C. 154(b) by 187 days.

(21) Appl. No.: 16/772,535

(22) PCT Filed: Dec. 14, 2018

(86) PCT No.: PCT/CN2018/121082
§ 371 (c)(1),
(2) Date: Jun. 12, 2020

(87) PCT Pub. No.: WO2019/114811
PCT Pub. Date: Jun. 20, 2019

(65) Prior Publication Data
US 2020/0385355 A1      Dec. 10, 2020

(30) Foreign Application Priority Data

Dec. 14, 2017    (CN) .......................... 201711370273.5
May 22, 2018    (CN) .......................... 201810519660.9

(51) Int. Cl.
*C07D 217/26*          (2006.01)
(52) U.S. Cl.
CPC ................................. *C07D 217/26* (2013.01)
(58) Field of Classification Search
CPC ....................................................... C07D 217/26
See application file for complete search history.

(56) References Cited

FOREIGN PATENT DOCUMENTS

| CN | 102143950 A | 8/2011 |
|----|-------------|--------|
| CN | 103435546   | 12/2013 |

(Continued)

OTHER PUBLICATIONS

Bansal R, Kumar G, Jain S, Puri B. Synthesis of Some 4-Substituted 1H-2, 3-Benzoxazin-1-ones. ChemInform. Mar. 28, 1989;20(13).

(Continued)

*Primary Examiner* — D Margaret M Seaman
(74) *Attorney, Agent, or Firm* — Thomas | Horstemeyer, LLP; Christopher Linder; Ragan Buckley

(57) ABSTRACT

The present application provides a method for synthesis of Roxadustat. A compound as represented by formula (VIII) is used as a raw material, and is reacted with phenol, a vinyl-containing ether, an acid, hydroxylamine, and then the product is reacted with glycine. In addition, the present application also provides intermediate compounds as represented by formula (IX), formula (XI), formula (XII), formula (IV), and formula (V) for synthesis of Roxadustat. Herein, details of the substituents involved in formula (VIII), formula (IX), formula (XI), and formula (XII) are stated in the description

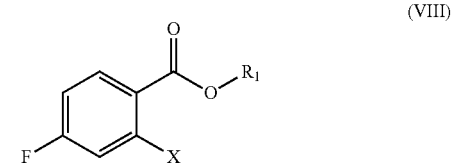

(VIII)

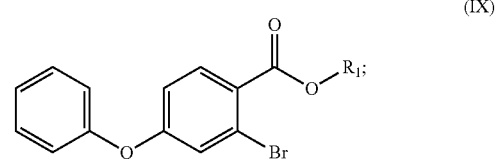

(IX)

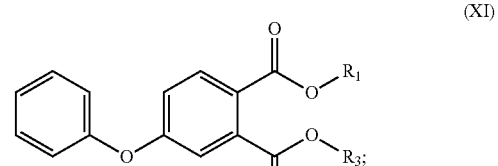

(XI)

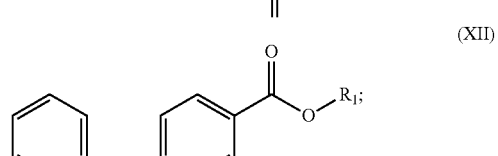

(XII)

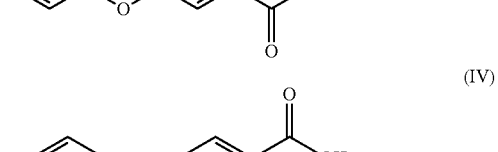

(IV)

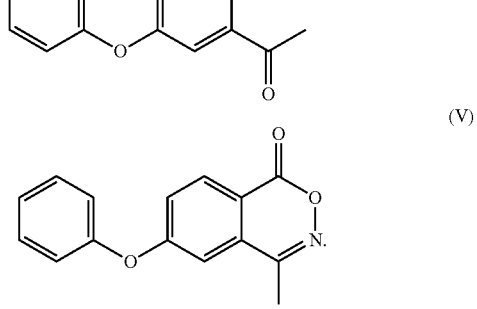

(V)

19 Claims, No Drawings

(56) References Cited

FOREIGN PATENT DOCUMENTS

| CN | 104024227 | | 9/2014 |
|----|-----------|---|--------|
| CN | 104892509 | | 9/2015 |
| CN | 105431439 | A | 3/2016 |
| CN | 106083720 | | 11/2016 |
| CN | 108794397 | | 11/2018 |
| JP | 2014524920 | A | 9/2014 |
| JP | 2015524409 | A | 8/2015 |
| WO | 2017/111787 | | 6/2017 |
| WO | 2017111787 | * | 6/2017 |
| WO | 2018/005591 | | 1/2018 |
| WO | 2018005591 | * | 1/2018 |
| WO | 2018/039310 | | 3/2018 |
| WO | 2018039310 | * | 3/2018 |
| WO | 2019114811 | A1 | 6/2019 |

OTHER PUBLICATIONS

First Examination Application No. from India IN202047024883 dated Feb. 3, 2021.

First Chinese Office Action Application No. CN201711370273.5 dated Jan. 28, 2021.

Abdou. W.M. et al. "Study of Insertion Reactions with Phosphorus Ylides on Reactions Between 4-(4-Methylphenyl)-2.3-Benzoxazin-1-One and Alkylidene Phosphoranes" European Journal of Organic Chemistry, No. No. 10, Apr. 16, 2002, pp. 1696-1701.

Kamel, A.A. "An Efficient Route to Phosphono-Substituted-Indoles and Quinolines from the Condensation of 2,3-and 2,4-Benzoxazin-1-Ones with a-Phosphonyl Carbanions" Phwphorus, Su/jitr and Silicon and the Related Elements, vol. 182, No. 4, Feb. 24, 2007, pp. 765-777.

International Search Report for PCT/CN2018/121082 dated Mar. 13, 2019.

Russian Examination Report for Application No. 2018383864 dated Sep. 30, 2020.

European Search Report for Application No. EP18889120 dated Oct. 21, 2020.

Office Action dated May 25, 2021 for Japanese Patent Application No. 2020-552089.

* cited by examiner

METHOD FOR SYNTHESIS OF ROXADUSTAT AND INTERMEDIATE COMPOUNDS THEREOF

CROSS-REFERENCE TO RELATED APPLICATIONS

This application is the 35 U.S.C. § 371 national stage application of PCT Application No. PCT/CN2018/121082, filed Dec. 14, 2018, where the PCT claims priority to, and the benefit of, CN Application No. 201810519660.9, filed May 22, 2018 and CN Application No. 201711370273.5, filed Dec. 14, 2017, all of which are herein incorporated by reference in their entireties.

TECHNICAL FIELD

The present application belongs to but is not limited to the field of medical technology, and more specifically, relates to a method for synthesis of Roxadustat and intermediate compounds thereof.

BACKGROUND ART

Roxadustat is an inhibitor of hypoxia-inducible factor-prolyl hydroxylase (HIF-PH), its chemical name is: 2-(4-hydroxy-1-methyl-7-phenoxy isoquinoline-3-carboxamido) acetic acid and its chemical structure is:

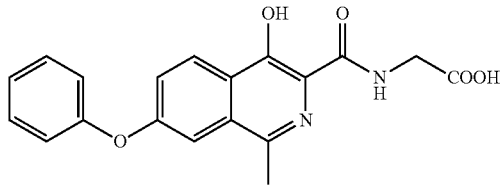 [SMILES: Cc1nc(C(=O)NCC(=O)O)c(O)c2ccc(Oc3ccccc3)cc12]

Fibrogen Inc. discloses a process for synthesis of Roxadustat in Chinese patent application CN1816527A. This patented process requires a large number of experimental steps to enable the introduction of the 1-position methyl group on the isoquinoline ring, and the introduction process usually requires noble metal catalysis and ultra-low temperature method that have high requirements on equipment; in particular, the third step has harsh reaction conditions, i.e. dicarboxylic acid and glycine are thoroughly ground together and then reacted with stirring at 210° C. in a molten state; the step of "ring-opening-ring-forming" to form isoquinoline has poor selectivity, which generates multiple positional isomers that require purification by column chromatography, the disadvantages include low yield, high cost, and unsuitability for large scale production.

Fibrogen Inc. discloses another process for synthesis of Roxadustat in Chinese patent application CN103435546A. In this method, the process of forming 5-bromophthalide and phenol into ether has high requirements on moisture, and ring-openings are easy to generate multiple by-products; both the second step of phthalide ring-opening and the step of methyl formation use precious metal Pd for the catalytic reaction, causing high cost; the step of methyl formation uses pressurized hydrogenation reduction, causing low industrial safety.

Shanghai Xunhe Pharmaceutical Technology Co., Ltd. discloses a method for synthesis of Roxadustat in Chinese patent application CN106478503A. The patented method has good selectivity and high yield. However, the multi-step intermediates in the reaction process are directly fed without purification, which is not conducive to quality control; and the use of "hydrazine" and "sulfonate" genotoxic impurities in the process increases the risk of safety of final products.

Beijing Beimetuo New Drug R & D Co., Ltd. discloses a method for synthesis of Roxadustat in its Chinese patent application CN104024227A. The patented method generates isoquinoline under mild reaction conditions, but requires a large number of experimental steps to perform the introduction of the 1-position methyl group on the isoquinoline ring, and the introduction process usually requires noble metal catalysis and ultra-low temperature methods. The yield in some reaction steps is low, and the column chromatography method is used for purification, the preparation cost is high, and it is not easy for scale production.

Shenzhen TargetRx, Inc. discloses a method for synthesis of Roxadustat in Chinese patent application CN106083720A. The patented method has mild reaction conditions, high reaction selectivity, no isomer formation, and no column purification. However, the use of a class of solvents, carbon tetrachloride, also results in the formation of the genotoxic impurity benzenesulfonate; the multi-step reaction intermediates are directly fed without purification, which is not conducive to quality control; the route of isoquinoline ring formation basically refers to the preparation route of the original drug.

Suzhou Miracpharma Technology Co., Ltd discloses a method for synthesis of Roxadustat in the Chinese patent application CN104892509A. In this patent method, by-products of the amino substitution product are easily generated during the process of introduction of the phenolic hydroxyl group into the phenyl process; the introduction of 4-position hydroxyl group on the isoquinoline ring adopts peroxyacetic acid oxidation method, which has some side reactions and has great safety risks in the industrial production process.

Shanghai Xunhe Pharmaceutical Technology Co., Ltd. discloses a method for synthesis of Roxadustat intermediates in its Chinese patent application CN06478503A. This patented method has short reaction steps, but it is not easy to obtain the dimethyl ketomalonate used, and a high temperature of nearly 200° C. is required in the ring-forming reaction, and thus the industrial operation is difficult.

SUMMARY OF THE INVENTION

Here is an overview of the subject matters of the detailed summary of the application. This summary is not intended to limit the scope of protection of the claims.

This application provides a method for synthesis of Roxadustat, including the following steps:

(a) a compound of formula (VIII) is reacted with phenol to obtain a compound of formula (IX)

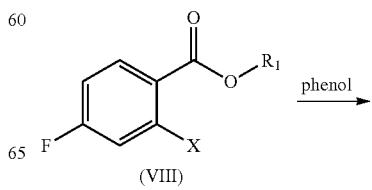
(VIII)

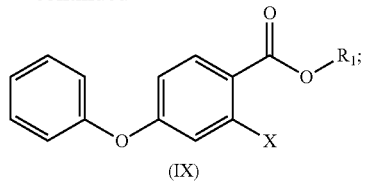

(b) the compound of formula (IX) is reacted with a compound of formula (X) to obtain a compound of formula (XI)

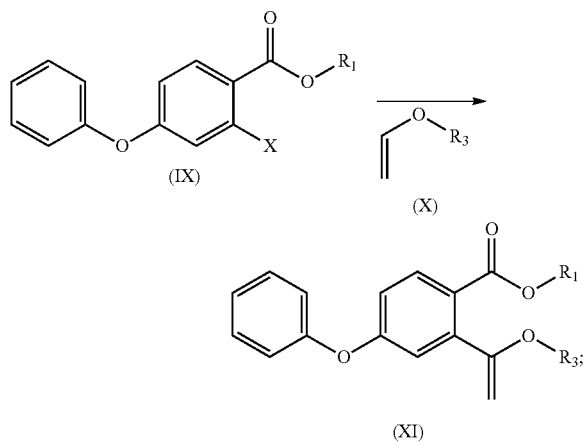

(c) the compound of formula (XI) is subjected to acid hydrolysis reaction to obtain a compound of formula (XII);

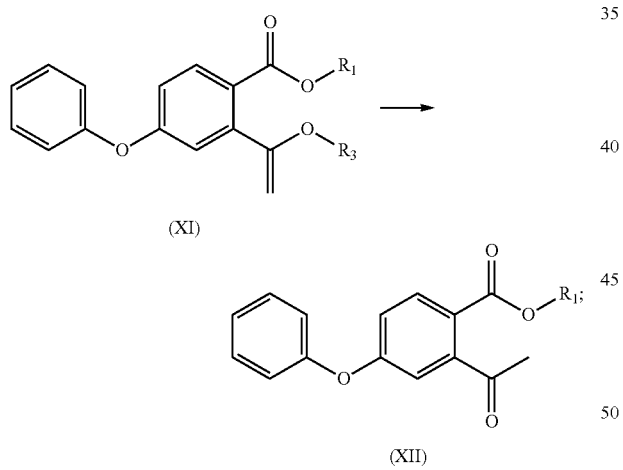

optionally, the compound of formula (XII) is subjected to hydrolysis reaction to obtain a compound of formula (IV) or a salt thereof;

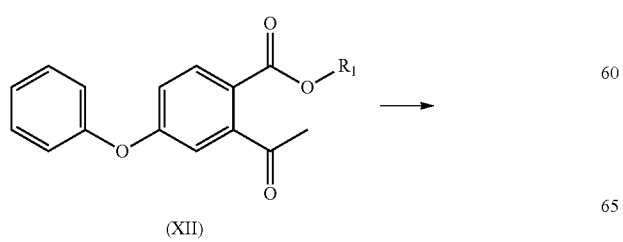

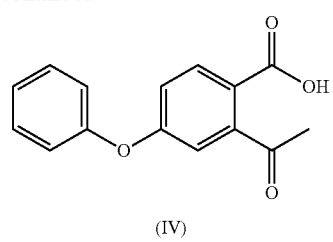

(d) the compound of formula (XII) or the compound of formula (IV) or a salt thereof is reacted with hydroxylamine to obtain a compound of formula (V);

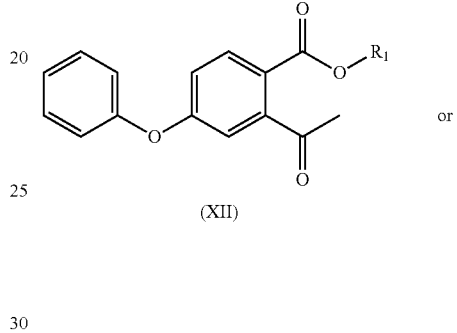

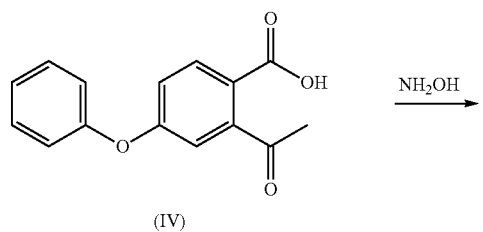

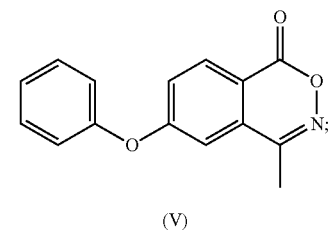

(e) the compound of formula (V) is reacted with a compound of formula (XIII) to obtain a compound of formula (XIV) or its tautomer or a mixture thereof;

-continued

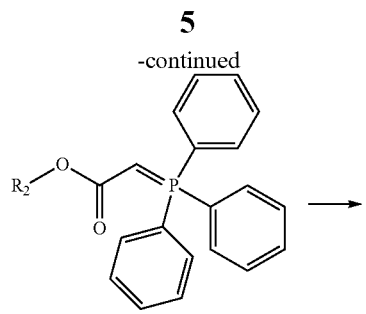

(XIII)

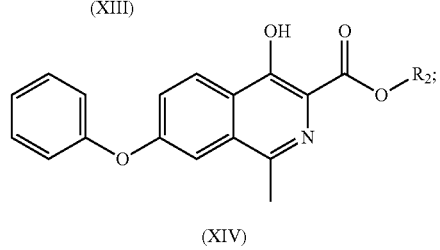

(XIV)

(f) the compound of formula (XIV) or its tautomer or a mixture thereof is reacted with glycine to obtain Roxadustat;

herein, $R_1$ in the compound of the formula (VIII), the compound of the formula (IX), the compound of the formula (XI), the compound of the formula (XII), and $R_2$ in the compound of the formula (XIII) and the compound (XIV) are each independently unsubstituted $C_1$-$C_4$ alkyl (e.g. methyl, ethyl, n-propyl, isopropyl, tert-butyl, sec-butyl or n-butyl), $C_1$-$C_4$ alkyl substituted with $C_1$-$C_4$ alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl)), $C_1$-$C_4$ alkyl substituted with substituted aromatic group (e.g. p-nitrobenzyl);

X in the compound of formula (VIII) and the compound of formula (IX) is bromine, iodine or chlorine;

$R_3$ in the compounds of formula (X) and (XI) is unsubstituted $C_1$-$C_4$ alkyl (e.g. methyl, ethyl, n-propyl, isopropyl, tert-butyl, sec-butyl or n-butyl), $C_1$-$C_4$ alkyl substituted with $C_1$-$C_4$ alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl), $C_1$-$C_4$ alkyl substituted with substituted aromatic group (e.g. p-nitrobenzyl).

On the other hand, this application provides intermediate compounds for the synthesis of Roxadustat, as shown in formula (IX):

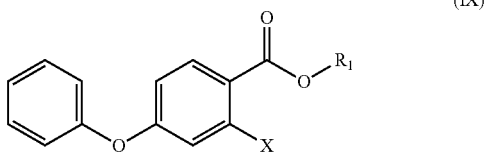

(IX)

$R_1$ in formula (IX) is unsubstituted $C_1$-$C_4$ alkyl group (e.g. methyl, ethyl, n-propyl, isopropyl, tert-butyl, sec-butyl, or n-butyl group), $C_1$-$C_4$ alkyl substituted with alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl), $C_1$-$C_4$ alkyl substituted with substituted aromatic group (e.g. p-nitrobenzyl);

X in formula (IX) is bromine, iodine or chlorine.

DETAILED SUMMARY

In the embodiments of the present application, the present application provides a method for synthesis of Roxadustat, including the following steps:

(a) a compound of formula (VII) is reacted with phenol to obtain a compound of formula (IX)

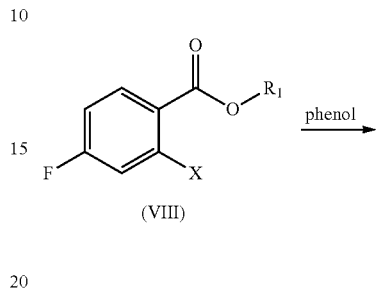

(VIII)

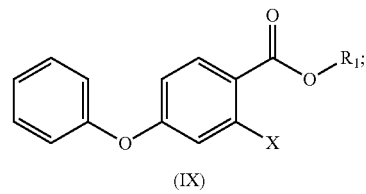

(IX)

(b) the compound of formula (IX) is reacted with a compound of formula (X) to obtain a compound of formula (XI)

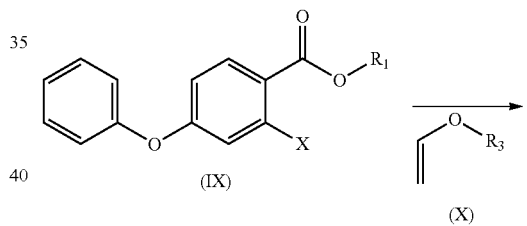

(IX)

(X)

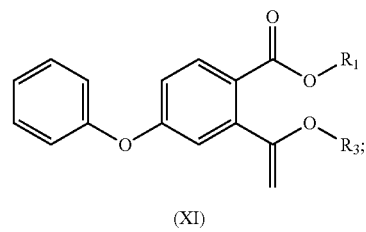

(XI)

(c) the compound of formula (XI) is subjected to acid hydrolysis reaction to obtain a compound of formula (XII);

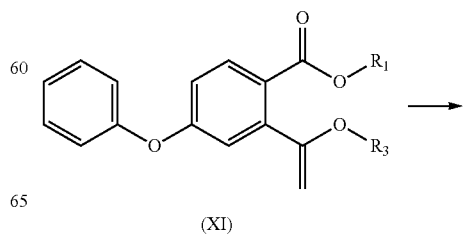

(XI)

-continued

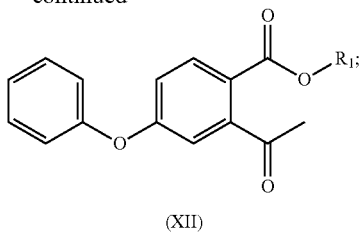

(XII)

optionally, the compound of formula (XII) is subjected to a hydrolysis reaction to obtain a compound of formula (IV) or a salt thereof;

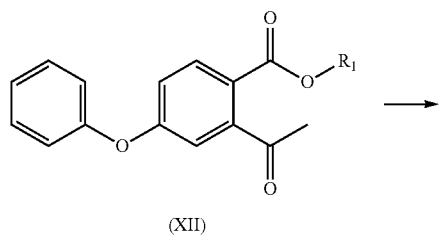

(XII)

(IV)

(d) the compound of formula (XII) or the compound of formula (IV) or a salt thereof is reacted with hydroxylamine to obtain a compound of formula (V);

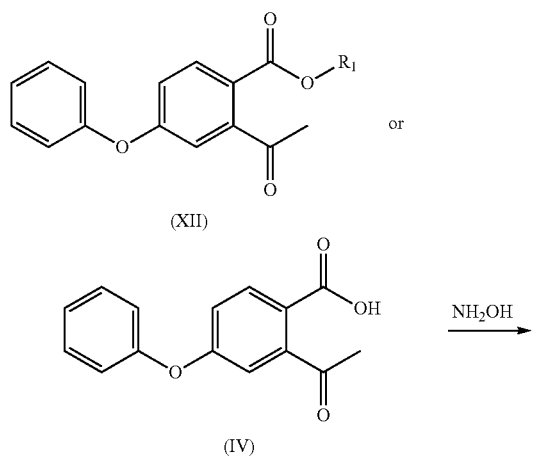

(XII)

(IV)

(V)

(e) the compound of formula (V) is reacted with a compound of formula (XIII) to obtain a compound of formula (XIV) or its tautomer or a mixture thereof;

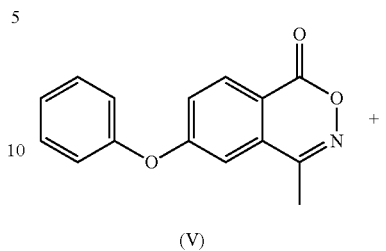

(V)

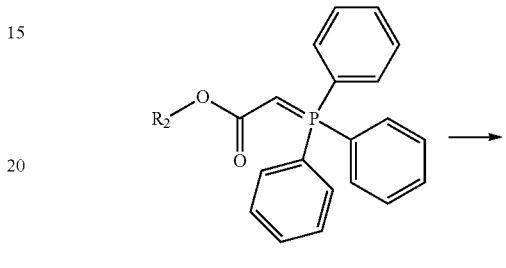

(XIII)

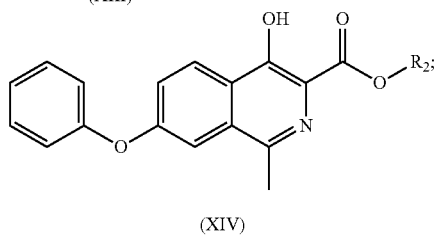

(XIV)

(f) the compound of formula (XIV) or its tautomer or a mixture thereof is reacted with glycine to obtain Roxadustat;

herein, $R_1$ in the compound of the formula (VIII), the compound of the formula (IX), the compound of the formula (XI), the compound of the formula (XII), and $R_2$ in the compound of the formula (XIII) and the compound (XIV) are each independently unsubstituted $C_1$-$C_4$ alkyl (e.g. methyl, ethyl, n-propyl, isopropyl, tert-butyl, sec-butyl or n-butyl), $C_1$-$C_4$ alkyl substituted with $C_1$-$C_4$ alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl)), $C_1$-$C_4$ alkyl substituted with substituted aromatic group (e.g. p-nitrobenzyl); preferably, $R_1$ and $R_2$ are each independently methyl, ethyl, n-propyl, isopropyl, tert-butyl, sec-butyl, n-butyl, methoxymethyl, benzyl, triphenylmethyl, phenoxymethyl, or p-nitrobenzyl; more preferably, both $R_1$ and $R_2$ are methyl;

X in the compound of formula (VIII) and the compound of formula (IX) is bromine, iodine or chlorine, more preferably bromine;

$R_3$ in the compounds of formula (X) and (XI) is unsubstituted $C_1$-$C_4$ alkyl group (e.g. methyl, ethyl, n-propyl, isopropyl, tert-butyl, sec-butyl or n-butyl), $C_1$-$C_4$ alkyl substituted with $C_1$-$C_4$ alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl), $C_1$-$C_4$ alkyl substituted with substituted aromatic group (e.g. p-nitrobenzyl); preferably, $R_3$ is methyl, ethyl, n-propyl, isopropyl, tert-butyl, sec-butyl, n-butyl, methoxymethyl, benzyl, triphenylmethyl, phenoxymethyl, or p-nitrobenzyl, more preferably, n-butyl.

In a preferred embodiment of the present application providing a method for synthesis of Roxadustat, $R_1$ in the compound of formula (VIII), compound of formula (IX), compound of formula (XI), compound of formula (XII), and $R_2$ in the compound of formula (XIII) and compound of formula (XIV) are each independently methyl, ethyl, n-propyl, isopropyl, t-butyl, sec-butyl, n-butyl, methoxymethyl, benzyl, triphenylmethyl, phenoxymethyl, or p-nitrobenzyl; more preferably, both $R_1$ and $R_2$ are methyl;

X in the compound of formula (VIII) and the compound of formula (IX) is bromine, iodine or chlorine, more preferably bromine;

$R_3$ in the compound of formula (X) and compound of (XI) is methyl, ethyl, n-propyl, isopropyl, t-butyl, sec-butyl, n-butyl, methoxymethyl, benzyl, triphenylmethyl, phenoxymethyl, or p-nitrobenzyl, more preferably, n-butyl.

In a more preferred embodiment of the present application providing a method for synthesis of Roxadustat, $R_1$ in the compound of formula (VIII), compound of formula (IX), compound of formula (XI), compound of formula (XII), and $R_2$ in the compounds of formula (XIII) and (XIV) are all methyl;

X in the compound of formula (VIII) and the compound of formula (IX) is bromine;

$R_3$ in the compounds of formula (X) and (XI) is n-butyl.

In an embodiment of the present application providing a method for synthesis of Roxadustat, the salt of the compound of formula (IV) includes but is not limited to an alkali metal salt or an alkaline earth metal salt, such as sodium salt, potassium salt, or calcium salt.

In a more preferred embodiment of the present application, the present application provides a method for synthesis of Roxadustat, including the following steps:

(1) methyl 2-bromo-4-fluorobenzoate is reacted with phenol to obtain a compound of formula (I)

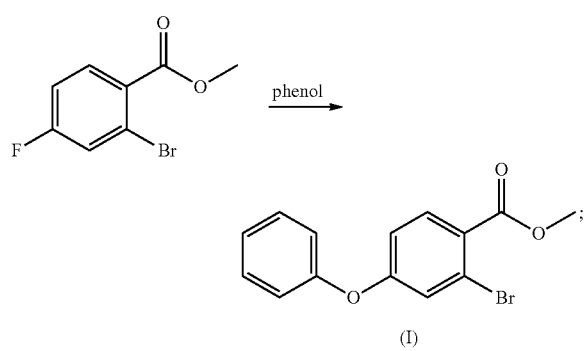

(2) the compound of formula (I) is reacted with butyl vinyl ether to obtain a compound of formula (II)

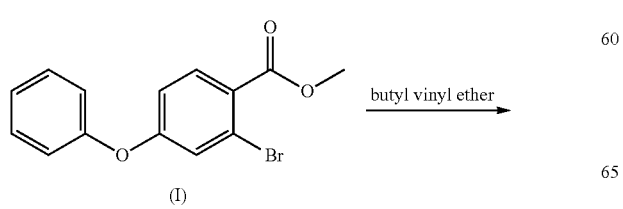

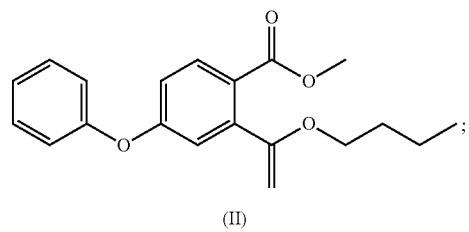

(3) the compound of formula (II) is subjected to an acid hydrolysis reaction to obtain a compound of formula (III);

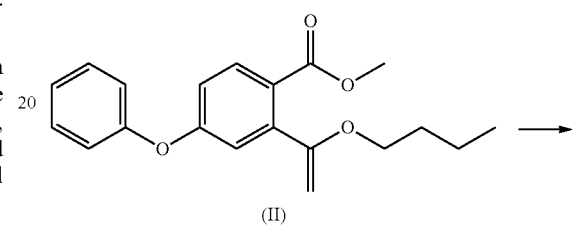

optionally, the compound of formula (III) is subjected to a hydrolysis reaction to obtain a compound of formula (IV) or a salt thereof;

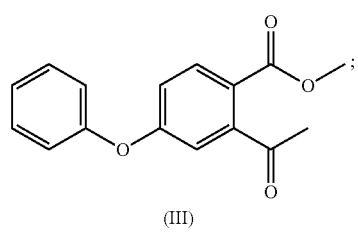

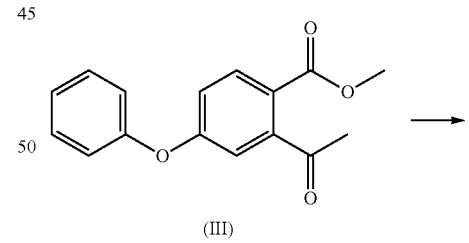

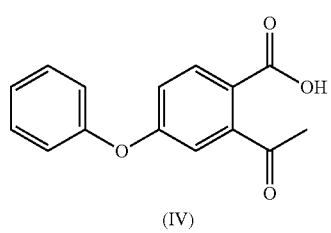

(4) the compound of formula (III) or the compound of formula (IV) or a salt thereof is reacted with hydroxylamine to obtain a compound of formula (V);

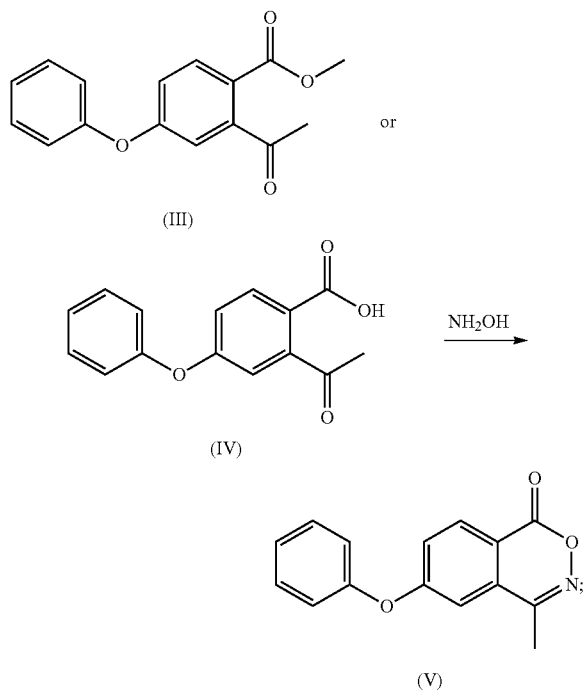

(5) the compound of formula (V) is reacted with a compound of formula (VI) to obtain a compound of formula (VII) or its tautomer or a mixture thereof;

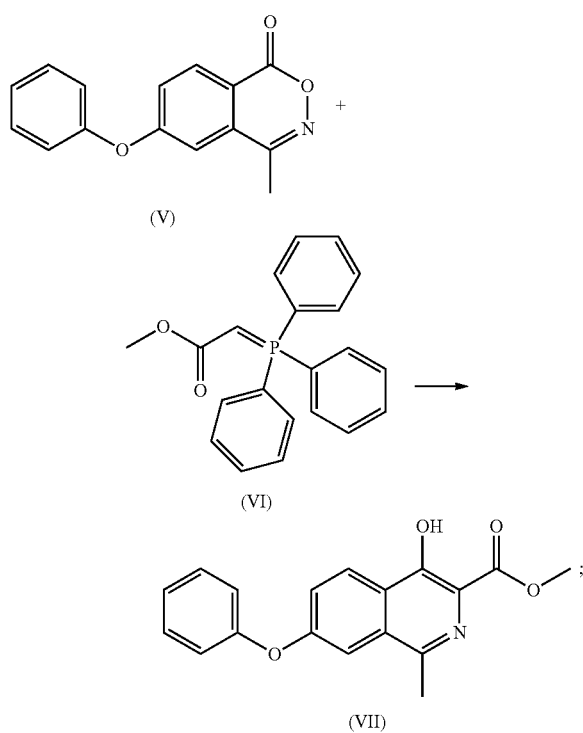

(6) the compound of formula (VII) or its tautomer or a mixture thereof is reacted with glycine to obtain Roxadustat.

In an embodiment of the present application providing a method for synthesis of Roxadustat, in step (a), the compound of formula (VIII) can be obtained by using 2-halo-4-fluorobenzoic acid, (said halo is bromo, chloro or iodo) and alcohol $R_1$—OH to perform a conventional esterification reaction, or obtained by firstly reacting 2-bromo-4-fluorobenzoic acid with an acyl chlorination reagent e.g. thionyl chloride, and then with alcohol $R_1$—OH; when X in the compound of formula (VIII) is bromine and $R_1$ is methyl, in step (1), methyl 2-bromo-4-fluorobenzoate can be obtained by using 2-bromo-4-fluorobenzoic acid and methanol by conventional esterification, or obtained by firstly reacting 2-bromo-4-fluorobenzoic acid with an acyl chlorination reagent e.g. thionyl chloride, and then with methanol.

In the embodiment of the present application providing a method for synthesis of Roxadustat, the reaction in step (a) or step (1) is carried out in the presence of a base; herein, the base is selected from alkali metal salts or alkali metal hydroxides, the alkali metal salts may be selected from alkali metal carbonates e.g. sodium carbonate, or potassium carbonate, and the metal hydroxides may be selected from sodium hydroxide and potassium hydroxide; the reaction in step (1) is carried out in an aprotic organic solvent selected from dimethylformamide (DMF), and acetonitrile, etc., preferably dimethylformamide (DMF).

In an embodiment of the present application providing a method for synthesis of Roxadustat, the reaction in step (b) or step (2) is carried out using a metal catalyst and a phosphorus ligand; herein, the metal catalyst may be selected from $Pd(OAc)_2$, $Pd(PPh_3)_4$, palladium chloride, 1,1'-bis(diphenylphosphino)ferrocene]palladium dichloride, $NiCl_2(PPh_3)_2$/Zn, $Cu/Al_2O_3$, $CoCl(PPh_3)_3$, preferably $Pd(OAc)_2$; the phosphorus ligand can be selected from triphenylphosphine, tri-o-tolylphosphine, preferably tri-o-tolylphosphine.

In an embodiment of the present application providing a method for synthesis of Roxadustat, the acid hydrolysis reaction in step (c) or step (3) is carried out in the presence of an acid; herein, the acid is selected from inorganic acids and organic acids, the inorganic acids are hydrochloric acid, sulfuric acid, or phosphoric acid, preferably hydrochloric acid; the organic acid may be selected from acetic acid and trifluoroacetic acid, preferably trifluoroacetic acid.

In the embodiment of the present application providing a method for synthesis of Roxadustat, the reaction in step (d) or step (4) is carried out in the presence of a base; herein, the base is selected from alkali metal salts, e.g. sodium carbonate, sodium acetate, or potassium carbonate, preferably sodium acetate.

In the embodiment of the present application providing a method for synthesis of Roxadustat, the reaction in step (e) or step (5) is carried out in a high-boiling organic solvent; herein, the high-boiling organic solvent is selected from one or more of toluene, xylene (or o-xylene, p-xylene), and anisole, etc., preferably xylene; the reaction is carried out in the presence of a base, herein, the base is selected from an organic base and an inorganic base, the organic base may be one or more selected from, for example, triethylamine, N,N-diisopropylethylamine (DIEA), and n-butylamine, preferably triethylamine; the inorganic base is one or more selected from potassium carbonate, sodium carbonate, potassium hydroxide, sodium hydroxide and the like, preferably potassium carbonate.

In an embodiment of the present application providing a method for synthesis of Roxadustat, in step (f) that the compound of formula (XIV) or its tautomer or a mixture thereof is reacted with glycine, or in step (6) that the compound of formula (VII) or its tautomer or a mixture thereof is reacted with glycine, the compound of formula (XIV) or its tautomer or mixture thereof, or the compound of formula (VII) or its tautomer or a mixture thereof can be reacted with glycine in the presence of sodium methoxide under normal or increased pressure to obtain Roxadustat.

On the other hand, this application provides intermediate compounds for synthesis of Roxadustat, as shown in formula (IX):

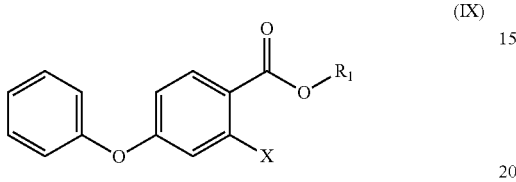

(IX)

$R_1$ in formula (IX) is an unsubstituted $C_1$-$C_4$ alkyl group (e.g. methyl, ethyl, n-propyl, isopropyl, tert-butyl, sec-butyl, or n-butyl), $C_1$-$C_4$ alkyl substituted with $C_1$-$C_4$ alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl), $C_1$-$C_4$ alkyl substituted with substituted aromatic group (e.g. p-nitrobenzyl); preferably, $R_1$ is methyl, ethyl, n-propyl, isopropyl, tert-butyl, sec-butyl, n-butyl, methoxymethyl, benzyl, triphenylmethyl, phenoxymethyl, or p-nitrobenzyl, more preferably, methyl;

X in formula (IX) is bromine, iodine, or chlorine, and more preferably, bromine.

In one embodiment of the present application, the present application provides intermediate compounds for synthesis of Roxadustat, as shown in formula (XI):

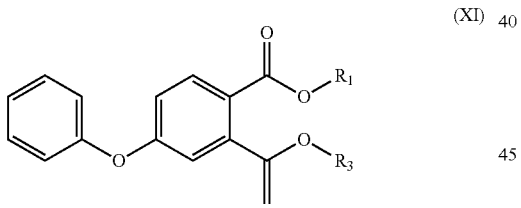

(XI)

$R_1$ in formula (XI) is unsubstituted $C_1$-$C_4$ alkyl group (e.g. methyl, ethyl, n-propyl, isopropyl, t-butyl, sec-butyl, or n-butyl), $C_1$-$C_4$ alkyl substituted with $C_1$-$C_4$ alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl), $C_1$-$C_4$ alkyl substituted with substituted aromatic group (e.g. p-nitrobenzyl); preferably, $R_1$ is methyl, ethyl, n-propyl, isopropyl, tert-butyl, sec-butyl, n-butyl, methoxymethyl, benzyl, triphenylmethyl, phenoxymethyl, or p-nitrobenzyl, more preferably, methyl;

$R_3$ in formula (XI) is unsubstituted $C_1$-$C_4$ alkyl (e.g. methyl, ethyl, n-propyl, isopropyl, tert-butyl, sec-butyl, or n-butyl group), $C_1$-$C_4$ alkyl substituted with $C_1$-$C_4$ alkoxy (e.g. methoxymethyl), $C_1$-$C_4$ alkyl substituted with unsubstituted aromatic group (e.g. benzyl, or triphenylmethyl), $C_1$-$C_4$ alkyl substituted with unsubstituted aromatic oxy group (e.g. phenoxymethyl), $C_1$-$C_4$ alkyl substituted with substituted aromatic group (e.g. p-nitrobenzyl); preferably, $R_3$ is methyl, ethyl, n-propyl, isopropyl, tert-butyl, sec-butyl, n-butyl, methoxymethyl, benzyl, triphenylmethyl, phenoxymethyl, or p-nitrobenzyl, more preferably, n-butyl.

In one embodiment of the present application, the present application provides intermediate compounds for synthesis of Roxadustat, as shown in formula (XII):

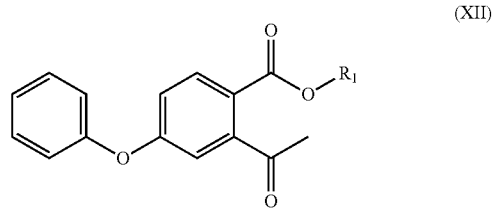

(XII)

$R_1$ in formula (XII) is an unsubstituted $C_1$-$C_4$ alkyl (e.g. methyl, ethyl, n-propyl, isopropyl, tert-butyl, sec-butyl, or n-butyl group), $C_1$-$C_4$ alkyl substituted with $C_1$-$C_4$ alkoxy (e.g. methoxymethyl), $C_1$-$C_4$ alkyl substituted with an unsubstituted aromatic group (e.g. benzyl, or triphenylmethyl), $C_1$-$C_4$ alkyl substituted with an unsubstituted aromatic oxy group (e.g. phenoxymethyl), $C_1$-$C_4$ alkyl substituted with a substituted aromatic group (e.g. p-nitrobenzyl); preferably, $R_1$ is methyl, ethyl, n-propyl, isopropyl, tert-butyl, sec-butyl, n-butyl, methoxymethyl, benzyl, triphenylmethyl, phenoxymethyl, or p-nitrobenzyl, more preferably, methyl.

In a preferred embodiment of the present application, the present application provides intermediate compounds for synthesis of Roxadustat, which is selected from one of the following compounds:

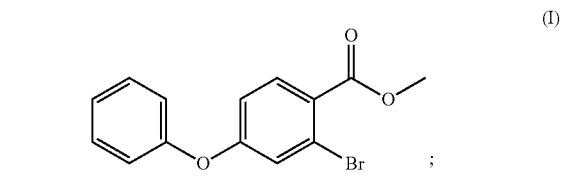

(I)

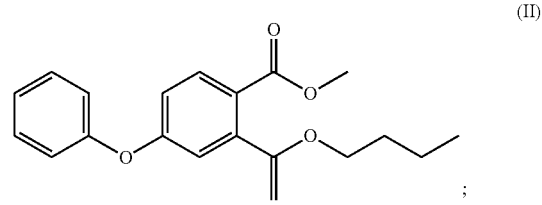

(II)

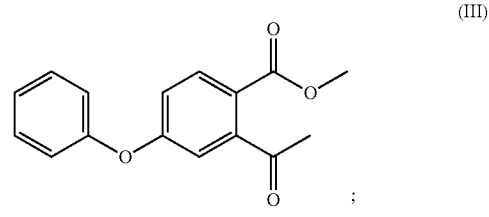

(III)

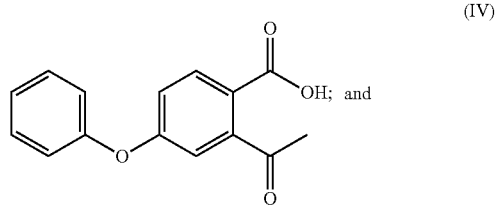

(IV)

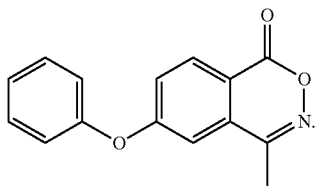

(V)

In a preferred embodiment of the present application, the present application provides intermediate compounds for synthesis of Roxadustat, selected from the salts of the following compounds:

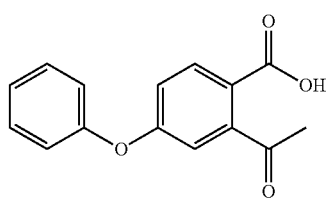

(IV)

herein, the salts include but are not limited to alkali metal salts or alkaline earth metal salts, e.g. sodium salts, potassium salts, or calcium salts.

SPECIFIC MODE FOR CARRYING OUT EMBODIMENTS

The embodiments of the present application are illustrated through the following examples. For those skilled in the art, these examples are only exemplary and do not constitute a limitation on the protection scope claimed by the present application.

In the examples of the present application, the nuclear magnetic instrument is: bruker Avance 400M, mass spectrometer: Waters tof mass LCT Premier.

Example 1. Preparation of methyl 2-bromo-4-fluorobenzoate

Methanol (182 ml) was added to the 500 ml of reaction flask and stirred, the temperature was cooled to 0-5° C. in an ice water bath, and thionyl chloride (17.6 ml) was slowly added dropwise. After the dropwise addition, the ice water bath was removed, 2-bromo-4-fluorobenzoic acid (14.00 g) was added, and the reaction was refluxed for 4 h. The temperature was cooled to room temperature, and methyl 2-bromo-4-fluorobenzoate (14 g, 94%) was obtained after removing the solvent by concentration. Mass: m/z 232.96 $[M+H]^+$.

Example 2. Preparation of Compound of Formula (I)

To a 250 ml of reaction flask was added dry DMF (40 ml), and, phenol (3.88 g), potassium carbonate (5.70 g), and methyl 2-bromo-4-fluorobenzoate (8.00 g) were added with stirring. The mixture was heated to 70° C. and reacted for 16 h, and the temperature was cooled to room temperature, water (40 ml) was added, the mixture was extracted with ethyl acetate (80 ml), the organic layer was washed with saturated sodium chloride solution, dried over anhydrous sodium sulfate, and concentrated to obtain the compound of formula (I) (10 g, 94%), which can also be used directly in the next step.

Mass: m/z 307.00$[M+H]^+$; $^1$H-NMR: (400 MHz, DMSO-$d_6$) 7.844 (d, 1H), 7.478 (m, 2H), 7.270 (m, 2H), 7.160 (m, 2H), 7.024 (m, 1H), 3.829 (s, 3H).

$^{13}$C-NMR: (400 MHz, DMSO-ds) 165.691, 160.760, 154.939, 133.705, 130.953, 130.953, 126.075, 125.716, 122.918, 122.595, 120.675, 120.675, 116.711, 52.884.

Example 3. Preparation of Compounds of Formula (II) and (III)

To a 100 ml of reaction flask was added acetonitrile (25 ml), and, the compound of formula (I) (5.00 g), butyl vinyl ether (3.26 g), tri-o-tolylphosphine (0.99 g), palladium acetate 0.11 g), DIPEA (diisopropylethylamine) (6.32 g) were added with stirring under purge nitrogen, and refluxed for 5 h. The solvent was removed by concentration at a cooled temperature, toluene (50 ml) was added, the mixture was filtered with stirring, and the filtrate was collected (the filtrate was concentrated to give compound (II)); 10% hydrochloric acid (40 ml) was added, and the mixture was stirred and reacted for 5 h. The layers were separated, and the organic layer was washed twice with saturated sodium bicarbonate solution (50 ml), dried over anhydrous sodium sulfate, and the organic layer was concentrated to give compound (III) (6.20 g, 88%).

Mass of the compound of formula (II): m/z 327.17$[M+H]^+$.

Mass of the compound of formula (III): m/z 271.01 $[M+H]^+$; $^1$H-NMR: (400 MHz, DMSO-$d_6$) 7.858 (d, 1H), 7.473 (t, 2H), 7.264 (t, 1H), 7.146 (t, 3H), 7.041 (t, 1H), 3.799 (s, 3H), 2.458 (s, 3H).

$^{13}$C-NMR: (400 MHz, DMSO-$d_6$) 166.421, 160.924, 155.136, 146.092, 132.483, 130.891, 130.891, 125.486, 122.203, 120.518, 120.518, 118.233, 115.757, 52.832, 30.428.

Example 3. Preparation of Compound of Formula (IV)

To a 100 ml four-necked flask was added 1,4-dioxane (40 ml), with stirring, the compound of formula (I) (5.00 g), 20% sulfuric acid solution (15 ml) was added and reacted at 55° C. for 16 h. The organic solvent was removed by concentration at cooled temperature, the residue was extracted with ethyl acetate (25 ml), washed twice with saturated sodium chloride solution (40 ml), dried over anhydrous sodium sulfate, and the organic layer was concentrated to give compound (IV) (4.48 g, 94%), compound (IV) (3.1 g, 66%) was obtained by recrystallization using ethyl acetate/n-hexane.

Mass: m/z 254.81$[M-H]^-$.

$^1$H-NMR: (400 MHz, CDCl$_3$) 7.740 (d, 1H), 7.450 (t, 2H), 7.282 (t, 1H), 7.101 (m, 4H), 1.850 (s, 3H).

Example 4. Preparation of Calcium Salt of Compound of Formula (IV)

To a 100 ml four-necked flask was added 1,4-sioxane (40 ml), and with stirring, the compound of formula (III) (5.00 g), 20% sulfuric acid solution (15 ml) was added and reacted at 55° C. for 16 h. The organic solvent was removed by concentration at a cooled temperature, the residue was extracted with ethyl acetate (25 ml), and water (30 ml) was added. The pH was adjusted to about 8.0 with 10% sodium hydroxide solution, and the mixture was warmed to 70-75° C. in water phase. A solution of calcium chloride (1.83 g) in water (28 ml) was added and the mixture was extracted twice with ethyl acetate (40 ml). The organic phase was concentrated to dryness under reduced pressure, isopropanol (10 ml) was added and stirred for 2 h, and the compound of formula (IV) as a white solid (4.2 g, 77%) was obtained by vacuum filtering.

$^1$H-NMR: (400 MHz, CD$_3$OD) 7.886 (d, 1H), 7.410 (t, 2H), 7.197 (t, 1H), 7.049 (d, 2H), 6.950 (d, 1H), 6.829 (d, 1H), 2.471 (s, 3H).

Example 5. Preparation of Compound of Formula (V)

To the 100 ml reaction flask was added anhydrous ethanol (30 ml), and with stirring the compound of formula (III) (6.20 g) or compound (IV) (5.92 g), hydroxylamine hydrochloride (3.53 g), anhydrous sodium acetate (3.76 g) were added and refluxed for 6 h. The mixture was cooled to room temperature to grow crystal for 1 h. After filtering under vacuum, water (30 ml) was added to the filter cake to beat for 1 h, the compound (3.56 g, 61%) as a white solid was obtained after vacuum filtering and drying. MP: 118° C.;

Mass: m/z 254.04[M+H]$^+$ $^1$H-NMR: (400 MHz, DMSO-d$_6$) 8.258 (d, 1H), 7.469 (m, 4H), 7.330 (t, 1H), 7.236 (t, 2H), 2.505 (s, 3H).

$^{13}$C-NMR: (400 MHz, DMSO-d$_6$) 163.556, 163.268, 154.682, 154.083, 131.411, 131.092, 129.937, 126.012, 123.010, 120.696, 120.696, 116.492, 114.309, 16.850.

Example 6. Preparation of Compound of Formula (V)

To a 100 ml of reaction flask was added anhydrous ethanol (40 ml), and with stirring, the calcium salt of the compound of formula (IV) (8 g), hydroxylamine hydrochloride (4.4 g), anhydrous sodium acetate (2.8 g) were added and refluxed for 6 h. The mixture was cooled to room temperature to grow crystal for 1 h and filtered under vacuum, water (40 ml) was added to the filter cake to beat for 1 h, the compound of formula (IV) as a white solid (5.7 g, 77%) was obtained after vacuum filtering and drying.

Example 7. Preparation of the Compound of Formula (VII)

To a 100 ml of reaction flask was added dry toluene (10 ml). With stirring, the compound of formula (V) (2.00 g), compound of formula (VI) (2.90 g) and triethylamine (0.40 g) were added and refluxed for 2 days under nitrogen atmosphere. The mixture was cooled to room temperature, and silica gel was added to absorb for 1 hour. After vacuum filtering, the filtrate was concentrated to dryness, then 10 ml of methanol was added, and with stirring, the crystal was precipitated to give 1.81 g of white solid with a yield of 74%. Through column chromatography (dichloromethane/n-hexane 3/7) the compound of formula (VI) was obtained, MP: 110° C.;

Mass: m/z 310.0[M+H]$^+$ $^1$H-NMR (400 MHz, DMSO-d) 11.521 (s, 1H), 8.354 (d, 1H), 7.511 (m, 4H), 7.234 (m, 3H), 3.968 (s, 3H), 2.660 (s, 3H).

$^{13}$C-NMR: (400 MHz, DMSO-d) 170.925, 158.919, 155.834, 154.564, 148.325, 132.073, 130.873, 130.873, 126.087, 125.161, 125.161, 123.387, 122.726, 120.082, 120.082, 118.966, 52.901, 21.875.

Example 8. Preparation of the Compound of Formula (VII)

To a 10 ml of reaction flask was added dry xylene (10 ml), and with stirring, the compound of formula (V) (2.00 g), compound of formula (VI) (2.90 g), potassium carbonate (0.54 g) was added and refluxed for 3 days under nitrogen atmosphere. The mixture was cooled to room temperature and filtered under vacuum. The filter cake was washed with water, then 10 ml of methanol was added, and with stirring the crystal was precipitated to give 1.7 g of the compound of formula (VII) with a yield of 70%.

Example 9. Preparation of Roxadustat

To a 100 ml of reaction flask was added methanol (3 ml). With stirring, the compound of formula (VII) (1.00 g), glycine (0.73 g), sodium methoxide (0.38 g) were added, and the mixture was heated to reflux until the reaction was complete. The reaction solution was cooled to room temperature, filtered under vacuum, and the filter cake was rinsed with methanol, and dried under vacuum. The filter cake was dissolved in water and washed with ethyl acetate. Acetic acid was added to the water layer, crystals were precipitated, stirred at room temperature, filtered under vacuum, washed with water and then cold acetone, and dried under vacuum to give Roxadustat with a yield of 82%.

Mass: m/z 353.04 [M+H]$^+$; $^1$H-NMR (400 MHz, DMSO-4) 13.304 (s, 1H), 12.861 (s, 1H), 9.093 (s, 1H), 8.282 (d, 1H), 7.604 (s, 1H), 7.493 (q, 3H), 7.258 (t, 1H), 7.182 (d, 2H), 4.063 (d, 2H), 2.698 (s, 3H).

$^{13}$C-NMR (400 MHz, DMSO-d$_6$) 171.261, 170.399, 158.270, 156.018, 153.297, 147.351, 131.882, 130.855, 130.855, 125.712, 125.031, 125.031, 123.964, 122.862, 119.981, 119.981, 112.573, 41.155, 21.975.

Although the embodiments disclosed in the present application are described above, the described contents are only the embodiments adopted to facilitate understanding of the present application, and are not intended to limit the present application. Any skilled person in this art to which this application belongs can make any modifications and changes in the form and details of implementation without departing from the spirit and scope disclosed in this application, but the patent protection scope of this application must still be defined by the appended claims.

What is claimed is:

1. A method for synthesis of Roxadustat, comprising the steps of:

(a) a compound of formula (VIII) is reacted with phenol to obtain a compound of formula (IX)

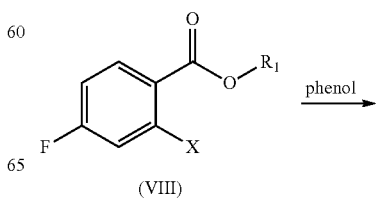
(VIII)

-continued

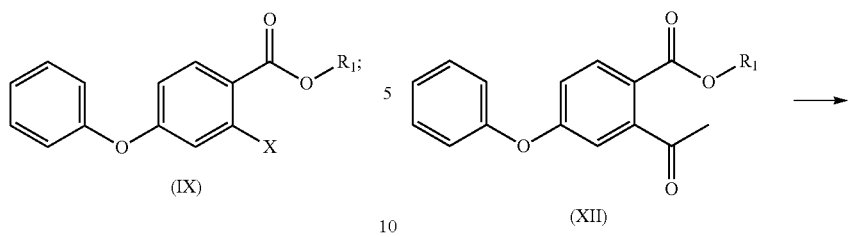

(b) the compound of formula (IX) is reacted with a compound of formula (X) to obtain a compound of formula (XI)

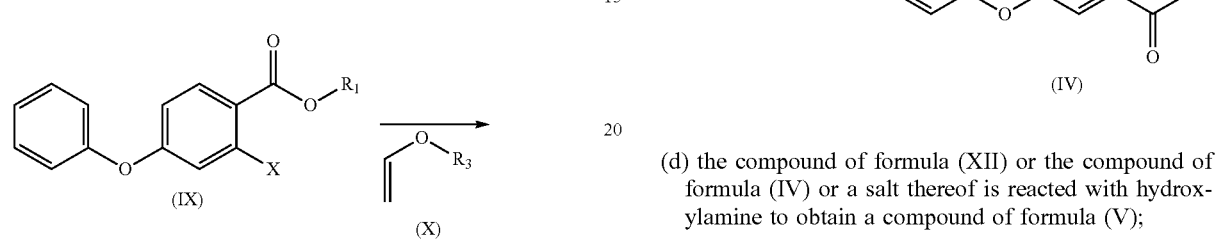

(c) the compound of formula (XI) is subjected to acid hydrolysis reaction to obtain a compound of formula (XII);

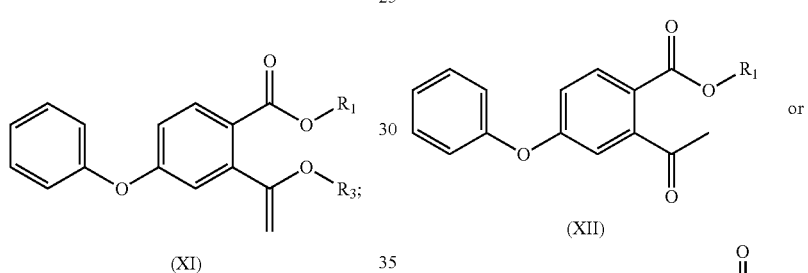

optionally, the compound of formula (XII) is subjected to hydrolysis reaction to obtain a compound of formula (IV) or a salt thereof;

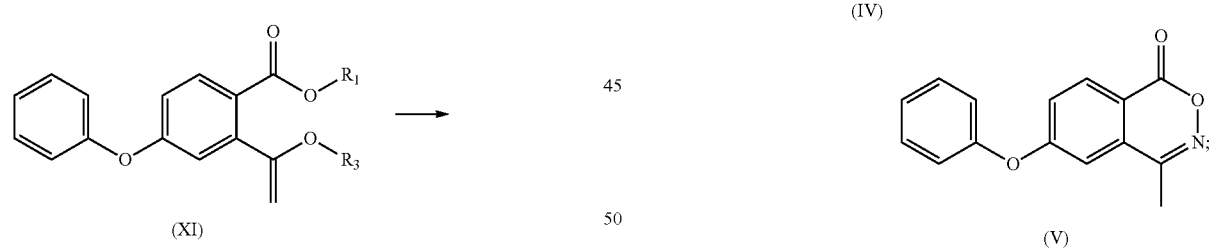

(d) the compound of formula (XII) or the compound of formula (IV) or a salt thereof is reacted with hydroxylamine to obtain a compound of formula (V);

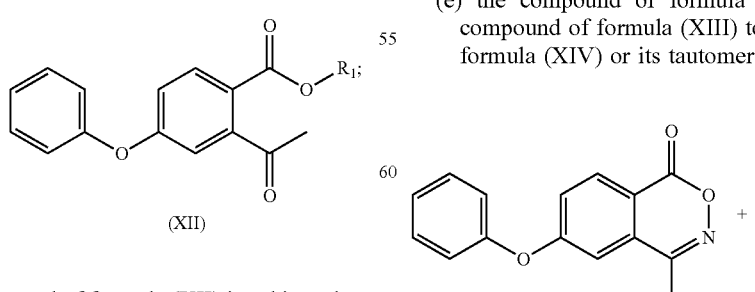

(e) the compound of formula (V) is reacted with a compound of formula (XIII) to obtain a compound of formula (XIV) or its tautomer or a mixture thereof;

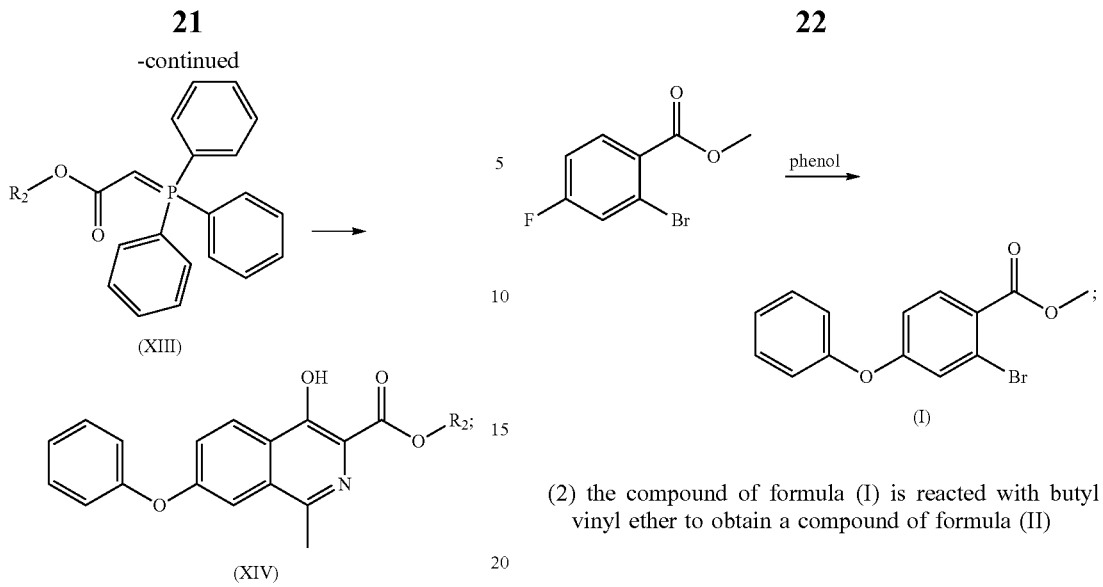

(XIII)

(XIV)

(f) the compound of formula (XIV) or its tautomer or a mixture thereof is reacted with glycine to obtain Roxadustat;

herein, $R_1$ in the compound of the formula (VIII), the compound of the formula (IX), the compound of the formula (XI), the compound of the formula (XII), $R_2$ in the compound of the formula (XIII) and the compound (XIV), and $R_3$ in the compound of formula (X) and compound of (XI) are each independently unsubstituted $C_1$-$C_4$ alkyl, $C_1$-$C_4$ alkyl substituted with $C_1$-$C_4$ alkoxy, $C_1$-$C_4$ alkyl substituted with unsubstituted aromatic group, $C_1$-$C_4$ alkyl substituted with unsubstituted aromatic oxy group, $C_1$-$C_4$ alkyl substituted with substituted aromatic group;

X in the compound of formula (VIII) and the compound of formula (IX) is bromine, iodine or chlorine.

2. The method for synthesis of Roxadustat according to claim 1, wherein, $R_1$ in the compound of formula (VIII), compound of formula (IX), compound of formula (XI), and compound of formula (XII), $R_2$ in the compound of formula (XIII) and compound of formula (XIV), and $R_3$ in the compound of formula (X) and compound of (XI) are each independently methyl, ethyl, n-propyl, isopropyl, t-butyl, sec-butyl, n-butyl, methoxymethyl, benzyl, triphenylmethyl, phenoxymethyl, or p-nitrobenzyl;

X in the compound of formula (VIII) and compound of formula (IX) is bromine, iodine or chlorine.

3. The method for synthesis of Roxadustat according to claim 1, wherein, $R_1$ in the compound of formula (VIII), compound of formula (IX), compound of formula (XI), and compound of formula (XII), $R_2$ in the compound of formula (XIII) and compound of formula (XIV) are methyl;

$R_3$ in the compound of formula (X) and compound of (XI) is n-butyl;

X in the compound of formula (VIII) and compound of formula (IX) is bromine.

4. A method for synthesis of Roxadustat, comprising the steps of:

(1) methyl 2-bromo-4-fluorobenzoate is reacted with phenol to obtain a compound of formula (I)

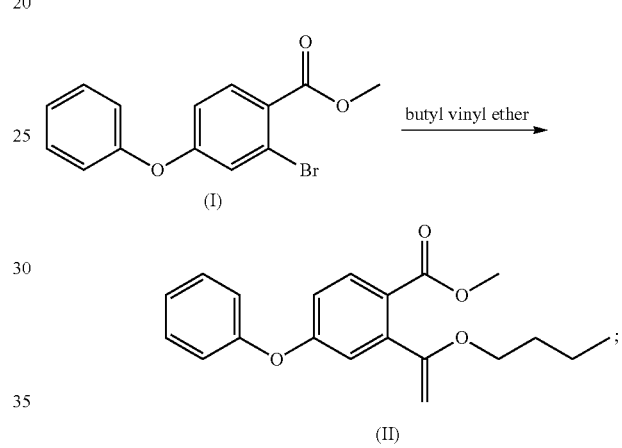

(2) the compound of formula (I) is reacted with butyl vinyl ether to obtain a compound of formula (II)

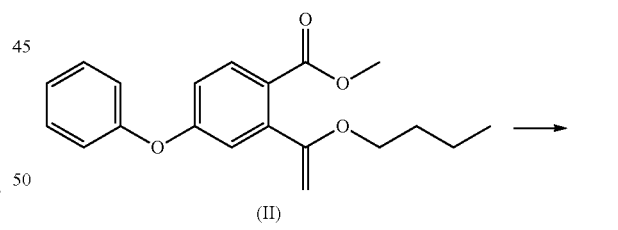

(3) the compound of formula (II) is subjected to an acid hydrolysis reaction to obtain a compound of formula (III);

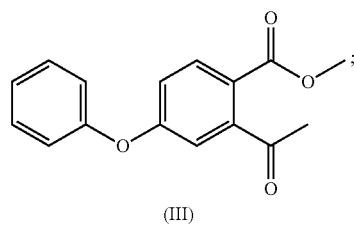

optionally, the compound of formula (III) is subjected to a hydrolysis reaction to obtain a compound of formula (IV) or a salt thereof;

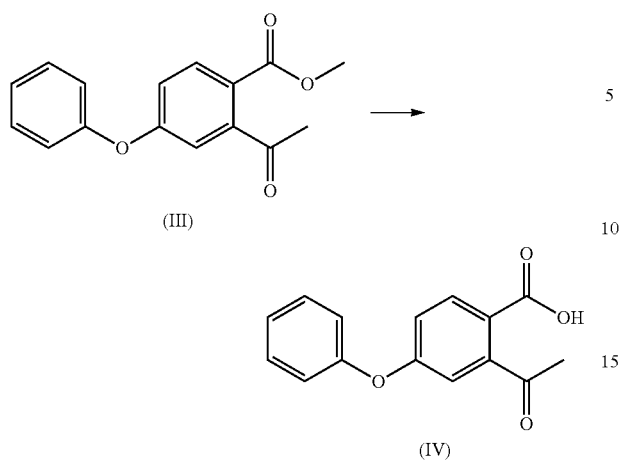

(III)

(IV)

(4) the compound of formula (III) or the compound of formula (IV) or a salt thereof is reacted with hydroxylamine to obtain a compound of formula (V);

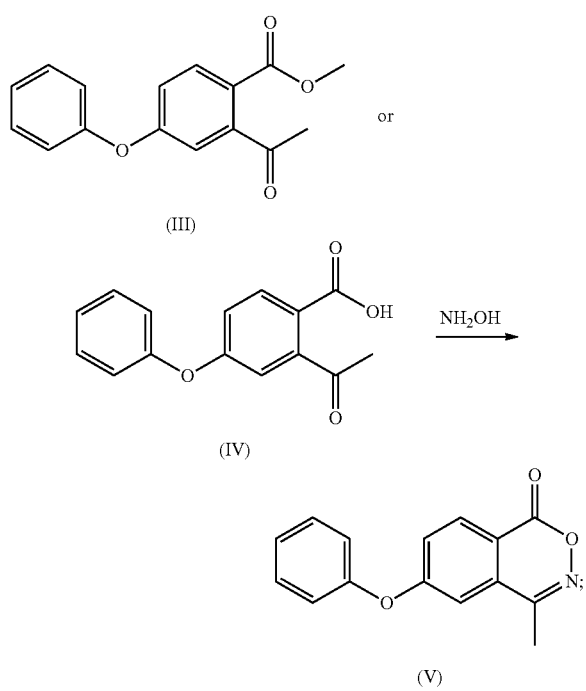

(III)

or (IV)

NH₂OH →

(V)

(5) the compound of formula (V) is reacted with a compound of formula (VI) to obtain a compound of formula (VII) or its tautomer or a mixture thereof;

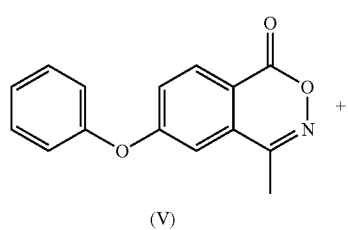

(V)

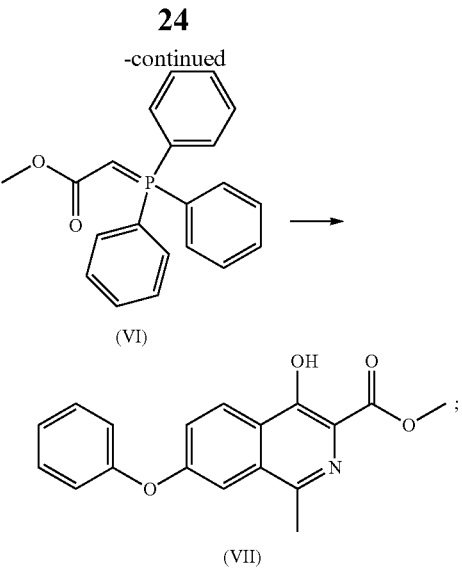

(VI)

(VII)

(6) the compound of formula (VII) or its tautomer or a mixture thereof is reacted with glycine to obtain Roxadustat.

5. The method for synthesis of Roxadustat according to claim 4, wherein in step (1), methyl 2-bromo-4-fluorobenzoate can be obtained by using 2-bromo-4-fluorobenzoic acid and methanol to perform a conventional esterification reaction, or obtained by firstly reacting 2-bromo-4-fluorobenzoic acid with an acyl chlorination reagent, and then with methanol.

6. The method for synthesis of Roxadustat according to claim 4, wherein the reaction in step (1) is carried out in the presence of a base; herein, the base is selected from alkali metal salts or alkali metal hydroxides, the alkali metal salts may be selected from alkali metal carbonates sodium carbonate, or potassium carbonate, the metal hydroxides may be selected from sodium hydroxide or potassium hydroxide.

7. The method for synthesis of Roxadustat according to claim 4, wherein the reaction in step (1) is carried out in an aprotic organic solvent selected from dimethylformamide (DMF), and acetonitrile.

8. The method for synthesis of Roxadustat according to claim 4, wherein the reaction in step (2) is carried out by using a metal catalyst and a phosphorus ligand; herein, the metal catalyst may be selected from $Pd(OAc)_2$, $Pd(PPh_3)_4$, palladium chloride, 1,1'-bis(diphenylphosphino)ferrocene] palladium dichloride, $NiCl_2(PPh_3)_2$/Zn, $Cu/Al_2O_3$, $CoCl(PPh_3)_3$; the phosphorus ligand can be selected from triphenylphosphine, tri-o-tolylphosphine, preferably tri-o-tolylphosphine.

9. The method for synthesis of Roxadustat according to claim 4, wherein the acid hydrolysis reaction in step (3) is carried out in the presence of an acid; hererin, the acid is selected from an inorganic acid or an organic acid, the inorganic acid is hydrochloric acid, sulfuric acid, or phosphoric acid; the organic acid may be selected from acetic acid and trifluoroacetic acid.

10. The method for synthesis of Roxadustat according to claim 4, wherein the reaction in step (4) is carried out in the presence of a base; herein, the base is selected from alkali metal salts, sodium carbonate, sodium acetate, or potassium carbonate.

11. The method for synthesis of Roxadustat according to claim 4, wherein the reaction in step (5) is carried out in a high-boiling organic solvent; herein, the high-boiling organic solvent is selected from toluene, xylene, and anisole; the reaction is carried out in the presence of a base, herein, the base is selected from an organic base and an inorganic base, the organic base is one or more selected from triethylamine, N,N-diisopropylethylamine (DIEA), and n-butylamine; the inorganic base is one or more selected from potassium carbonate, sodium carbonate, potassium hydroxide and sodium hydroxide.

12. An intermediate compound for synthesis of Roxadustat, as shown in formula (IX), formula (XI), or formula (XII):

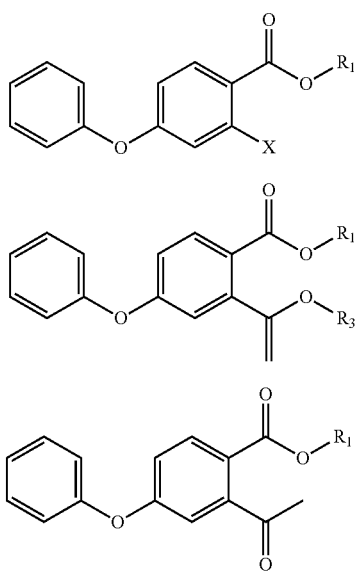

wherein, $R_1$ in the formula (IX), formula (XI), and formula (XII) is each independently unsubstituted $C_1$-$C_4$ alkyl, $C_1$-$C_4$ alkyl substituted with $C_1$-$C_4$ alkoxy, $C_1$-$C_4$ alkyl substituted with unsubstituted aromatic group, $C_1$-$C_4$ alkyl substituted with unsubstituted aromatic oxy group, $C_1$-$C_4$ alkyl substituted with substituted aromatic group;

$R_3$ in the formula (XI) is each independently unsubstituted $C_1$-$C_4$ alkyl, $C_1$-$C_4$ alkyl substituted with $C_1$-$C_4$ alkoxy, $C_1$-$C_4$ alkyl substituted with unsubstituted aromatic group, $C_1$-$C_4$ alkyl substituted with unsubstituted aromatic oxy group, $C_1$-$C_4$ alkyl substituted with substituted aromatic group;

X in the formula (IX) is bromine, iodine or chlorine;

with the proviso that when X is bromine or chlorine, $R_1$ is not methyl.

13. An intermediate compound for synthesis of Roxadustat, selected from the following compound of formula (II), compound of formula (III), compound of formula (IV) or a salt thereof, and compounds of formula (V):

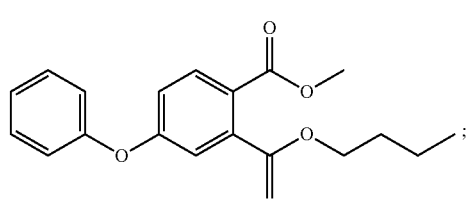

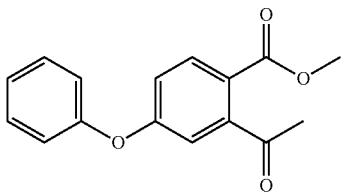

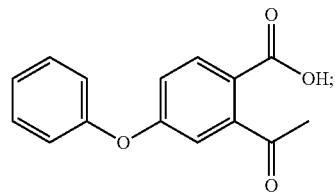

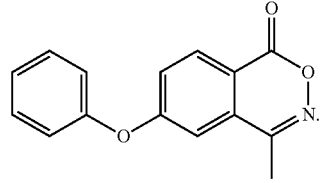

14. The method for synthesis of Roxadustat according to claim 1, wherein the reaction in step (a) is carried out in the presence of a base; herein, the base is selected from alkali metal salts or alkali metal hydroxides, the alkali metal salts may be selected from alkali metal carbonates sodium carbonate, or potassium carbonate, the metal hydroxides may be selected from sodium hydroxide or potassium hydroxide.

15. The method for synthesis of Roxadustat according to claim 1, wherein the reaction in step (a) is carried out in an aprotic organic solvent selected from dimethylformamide (DMF), and acetonitrile.

16. The method for synthesis of Roxadustat according to claim 1, wherein the reaction in step (b) is carried out by using a metal catalyst and a phosphorus ligand; herein, the metal catalyst may be selected from $Pd(OAc)_2$, $Pd(PPh_3)_4$, palladium chloride, 1,1'-bis(diphenylphosphino)ferrocene] palladium dichloride, $NiCl_2(PPh_3)_2$/Zn, $Cu/Al_2O_3$, $CoCl(PPh_3)_3$; the phosphorus ligand can be selected from triphenylphosphine, tri-o-tolylphosphine.

17. The method for synthesis of Roxadustat according to claim 1, wherein the acid hydrolysis reaction in step (c) is carried out in the presence of an acid; hererin, the acid is selected from an inorganic acid or an organic acid, the inorganic acid is hydrochloric acid, sulfuric acid, or phosphoric acid; the organic acid may be selected from acetic acid and trifluoroacetic acid.

18. The method for synthesis of Roxadustat according to claim 1, wherein the reaction in step (d) is carried out in the presence of a base; herein, the base is selected from alkali metal salts, such as sodium carbonate, sodium acetate, or potassium carbonate.

19. The method for synthesis of Roxadustat according to claim 1, wherein the reaction in step (e) is carried out in a high-boiling organic solvent; herein, the high-boiling organic solvent is selected from toluene, xylene, and anisole; the reaction is carried out in the presence of a base, herein, the base is selected from an organic base and an inorganic base, the organic base is one or more selected from triethylamine, N,N-diisopropylethylamine (DIEA), and n-butylamine; the inorganic base is one or more selected from potassium carbonate, sodium carbonate, potassium hydroxide and sodium hydroxide.

* * * * *